(12) United States Patent
Burkett

(10) Patent No.: US 6,830,743 B1
(45) Date of Patent: Dec. 14, 2004

(54) IN VIVO STAIN COMPOUNDS AND METHODS OF USE TO IDENTIFY DYSPLASTIC TISSUE

(75) Inventor: Douglas D. Burkett, Phoenix, AZ (US)

(73) Assignee: Zila Biotechnology, Inc., Phoenix, AZ (US)

( * ) Notice: Subject to any disclaimer, the term of this patent is extended or adjusted under 35 U.S.C. 154(b) by 0 days.

(21) Appl. No.: 09/937,632

(22) PCT Filed: Jan. 31, 2000

(86) PCT No.: PCT/US00/02602

§ 371 (c)(1),
(2), (4) Date: Jan. 22, 2002

(87) PCT Pub. No.: WO01/54696

PCT Pub. Date: Aug. 2, 2001

(51) Int. Cl.[7] .......................... A61B 10/00; C07D 279/18
(52) U.S. Cl. ............................. 424/9.7; 424/9.8; 544/37
(58) Field of Search ...................... 544/37, 56; 424/9.8, 424/9.7, 9.1

(56) References Cited

U.S. PATENT DOCUMENTS

| | | | | | |
|---|---|---|---|---|---|
| 4,321,251 | A | * | 3/1982 | Mashberg | 424/9.7 |
| 5,372,801 | A | * | 12/1994 | Malmros et al. | 424/9.7 |
| 6,153,399 | A | * | 11/2000 | Fujishiro et al. | 435/28 |
| 6,327,904 | B1 | * | 12/2001 | Oldenettel | 73/146 |
| 6,417,003 | B1 | * | 7/2002 | Cipriani | 436/64 |
| 6,649,144 | B1 | * | 11/2003 | Burkett et al. | 424/9.1 |

OTHER PUBLICATIONS

Galey, Laurent, "Phenothiazinium derivative having an antiparasitic and biological activity", CA136:226765, 2002.*

* cited by examiner

*Primary Examiner*—Deborah C. Lambkin
(74) *Attorney, Agent, or Firm*—Drummond & Duckworth

(57) ABSTRACT

Compounds having the structural formula (A) wherein X is hydrogen, methyl, or Y; Y is —NH—R or hydrogen; and R is methyl or formula (B) are useful as in vivo stains for the detection of dysplastic tissue.

5 Claims, 1 Drawing Sheet

IN VIVO STAIN COMPOUNDS AND METHODS OF USE TO IDENTIFY DYSPLASTIC TISSUE

This invention relates to new biological stain compounds that are useful for human in vivo topical application.

In another aspect, the invention concerns in vivo methods of using such novel compounds to identify suspect dysplastic, i.e., abnormal, tissue.

In yet another and further respect, the invention pertains to new compounds and in vivo diagnostic methods of use thereof, which are specially adapted for detecting suspect dysplastic oral tissue, especially cancerous and precancerous tissue.

The various embodiments of the invention and the practice thereof will be apparent to those skilled in the art, from the following detailed description thereof and the drawing, in which:

BACKGROUND OF THE INVENTION

Figure 1:
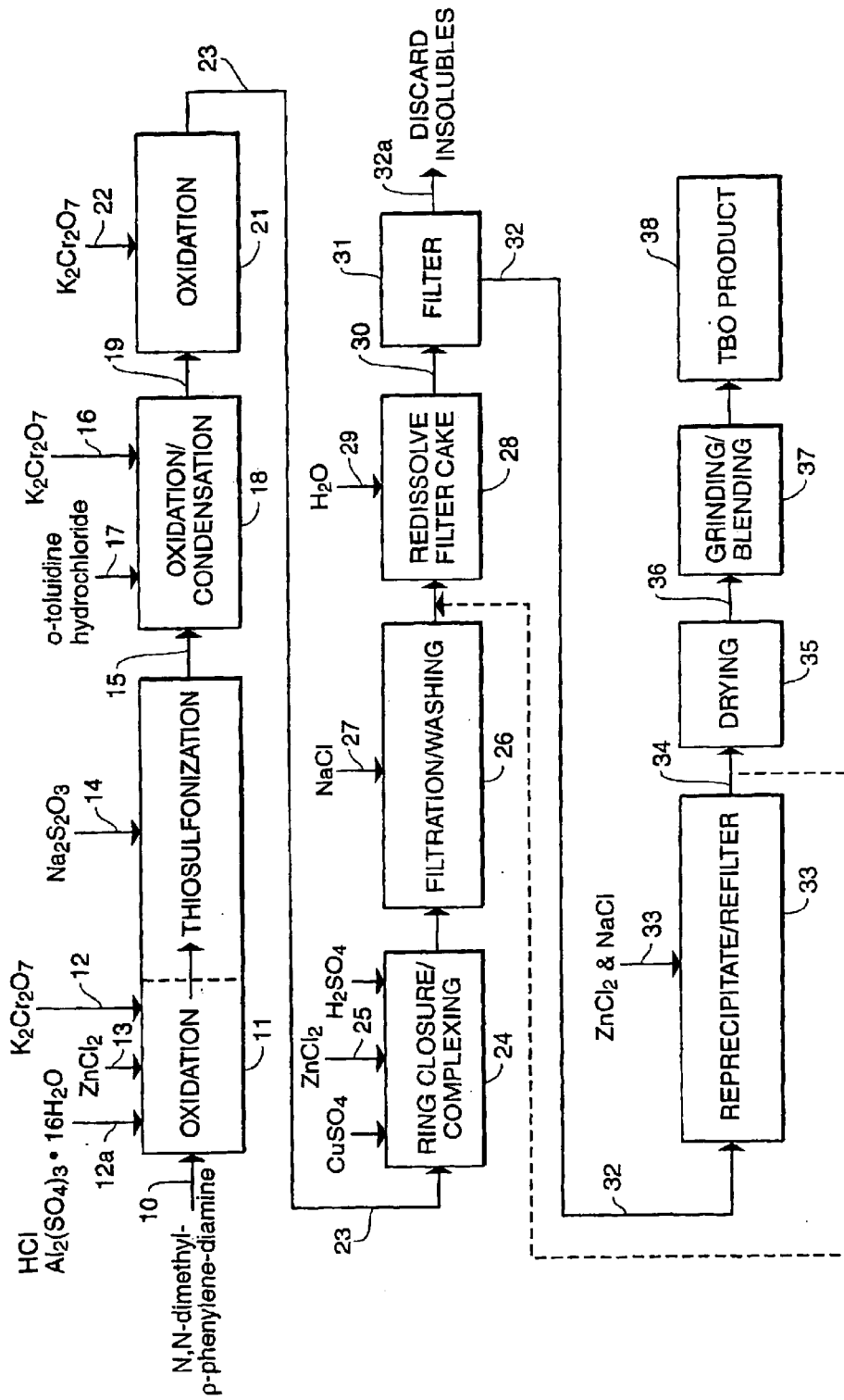
FIG. 1 is a process flow diagram, depicting a process for synthesizing the novel compounds of the present invention.

Most eptitheleal lesions result from trauma. However, other lesions are dysplastic tumors, some of which may be benign, but some of which may be either cancerous or precancerous. In addition, many dysplastic lesions are small and easily missed on routine visual examination by clinicians, especially those within body cavities such as the oral cavity.

An in vivo diagnostic test is known which identifies and delineates suspect dysplastic tissue. This screening test, employing toluidine blue 0 (tolonium chloride) as an in vivo stain, which selectively stains cancerous and precancerous tissue, is generally described in the U.S. Pat. No. 4,321,251 to Mashberg and in the U.S. Pat. No. 5,372,801 to Tucci et al. Once a suspect dysplastic lesion is identified by the Mashberg protocol, a regular biopsy sample can be taken and subjected to histological examination, to confirm whether the lesion is malignant or precancerous. Kits for performing this test, containing premixed dye and rinse solutions in the proper quantities and concentrations, are licensed by Zila, Inc. and are available commercially in several countries under the trademarks ORASCREEN® and ORATEST®.

BRIEF DESCRIPTION OF THE INVENTION

I have now discovered new compounds which are useful as in vivo biological stains for selectively staining and delineating dysplastic tissue. These compounds have the structural formula

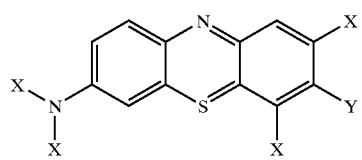

wherein X is hydrogen, methyl or Y; Y is —NH—R or hydrogen;

and R is methyl or

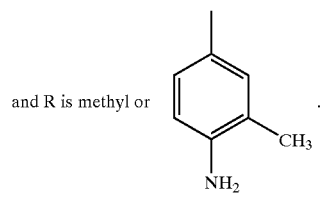

Illustratively, these compounds include

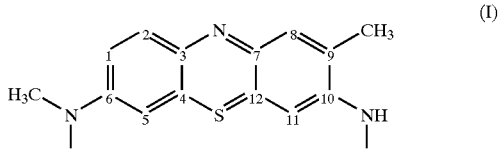
(I)

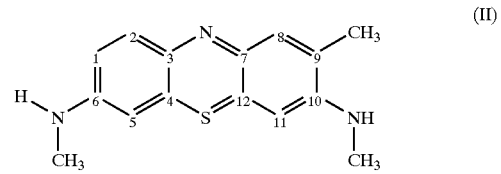
(II)

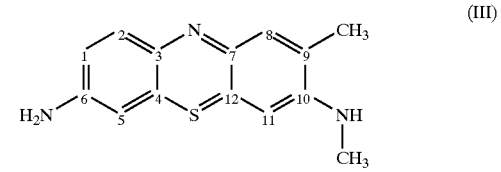
(III)

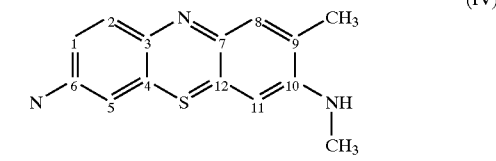
(IV)

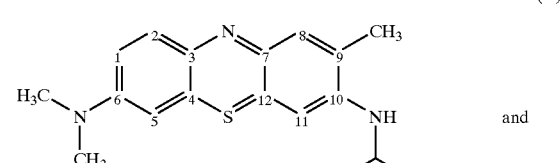
(V) and

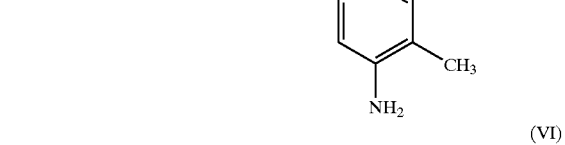
(VI)

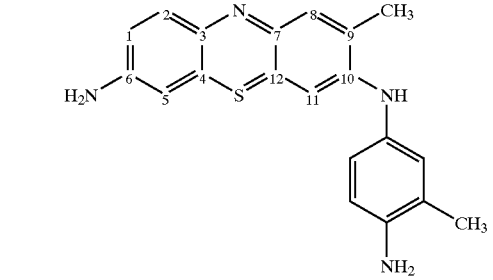

Brief Description of the Manufacturing Process

The compounds of the invention are synthesized by a process similar (with exceptions noted below) to the process described in U.S. Pat. No. 418,055, issued Nov. 30, 1889, to Dandliker et al. for the production of toluidine blue O ("TBO"). The Dandliker Synthesis is a series of three oxidation steps: (1) oxidation of N,N-dimethyl-p- phenylenediamine, e.g., with potassium dichromate, to form 2-amino-5-dimethylaminophenyl thiosulfonic acid; (2) condensation of the thiosulfonic acid with o-toluidine, to form the corresponding indamine-thiosulfonic acid; and (3) ring closure of the indamine-thiosulfonic acid, e.g., in the presence of a complexing agent at boiling temperature for about 30 minutes, to form toluidine blue O. The reaction mixture is then cooled and the reaction product of the ring-closure reaction complex is salted out. Purification of the complex may be accomplished by repeated re-solution and re-precipitation.

The processes for preparing the compounds of the present invention differ from the Dandliker Synthesis in that the complexing agent is added prior to the third oxidation step, preferably during the first oxidation step and the novel products of the present invention are isolated and separated from the precipitated complex by High Performance Liquid Chromatography (HPLC).

Brief Description of the Use of the Use of the Products for the Detection of Epitheleal Cancer The novel compounds of the invention are employed in accordance with the Mashberg Protocol, to selectively stain dysplastic eptitheleal tissue, except that each of these compounds is used instead of toluidine blue O. Thus, the present invention also contemplates a method for human in vivo detection of dysplastic tissue, which includes the step of applying to human epitheleal tissue a composition which includes one of the above-described new products or mixtures thereof.

Detailed Description of the Manufacturing Process for Preparing the Products of the Present Invention FIG. 1 is a process flow diagram which depicts a process for preparing the novel compounds of the present invention.

The starting material 10 for the synthesis is commercially-available, high-purity N,N-dimethyl-a-phenylene diamine.

Formation of First Reaction Mixture

An aqueous solution of the starting material 10 is oxidized 11, preferably at less than 10° C., especially at less than about 5° C., by reaction with a suitable oxidizing agent 12, e.g., potassium dichromate 12, in the presence of acid, aluminum sulfate and a reagent, 13 (which is believed to complex the intermediate(s) and is used in a later stage of the process to complex the reaction product components, e.g., zinc chloride. Then, a source of thiosulfate ions 14, e.g., sodium thiosulfate, is added to form a first reaction mixture 15 containing the first intermediate, 2-Amino-5-dimethylaminophenyl thiosulfonic acid.

Formation of Second Reaction Mixture

The first reaction mixture 15 is then further reacted, preferably at a temperature of not greater than about 10° C., with additional oxidizing agent 16, e.g., potassium dichromate, and o-toluidine hydrochloride 17, in a condensation step 16 to form the second intermediate, a condensation product, indamine thiosulfonic acid, in the second reaction mixture 19.

Formation of Third Reaction Mixture

The second reaction mixture 19 is then further oxidized 21, preferably by addition of a suitable oxidizing agent 22, e.g., potassium dichromate, at a temperature of not greater than about 10° C. This is followed by the addition of copper sulfate, zinc chloride complexing agent, acid and heating to 100° C. to effect closure of the indamine ring, forming a final reaction product in a third reaction mixture 24. At this point the reaction product is separated from the third reaction mixture and purified.

Separation/Purification of Third Reaction Product

For example, in the presently preferred embodiment of the process of the present invention, the reaction product is precipitated from the third reaction mixture by complexation 24 with a suitable complexing agent 25, e.g., zinc chloride, to form the complex zinc chloride double salt. The precipitate is filtered 26 from the liquid phase and washed with sodium chloride solution 27. The washed filter cake is then redissolved 28 in a critical[1] volume of water 29 to form a reaction product solution 30, which is then filtered 31 to remove undissolved solids 32a, which are discarded. Zinc Chloride, followed by a critical[2] volume/concentration of sodium chloride 33 is then added to the filtrate 32 to again precipitate the zinc chloride double salt.

[1] If too much water is used it prevents isolation of the reaction product. If too little water is used (1) all of the reaction product does not get dissolved, reducing the yield and (2) it decreases the purity of the product.

[2] If too little sodium chloride is used, all of the product will not be salted out, reducing yield. If too much sodium chloride is used it will cause impurities to precipitate out along with the reaction product, decreasing the purity of the product.

The double salt product is separated from the mixture by filtration, to yield a filter cake 34. As indicated by the dashed line 35, the filter cake 34 can be redissolved, filtered, re-precipitated and reisolated multiple times to achieve the desired degree of purity and yield of the double salt complex reaction product. The final purified filter cake complex product 34 is then dissolved in water and the novel compounds of the present invention are isolated and separated by HPLC procedures, described below.

WORKING EXAMPLES

The following examples are presented to illustrate the practice of the invention in such terms as to enable those skilled in the art to make the novel compounds of the invention and to practice the novel diagnostic methods using such new compounds, which together form the various embodiments of the invention, and to indicate to those skilled in the art the presently known best modes for practicing the various embodiments of the invention. These examples are presented as illustrative only and not as indicating limits on the scope of the invention, which is defined only by the appended claims.

Example 1

Manufacturing Process

This example illustrates the exact procedures for preparing a batch of dye product complex and the separation of the novel compounds of the invention from the complex product by HPLC.

Preparation of Raw Materials Solutions

Equipment/supplies:

A. Ohaus IP15KS Balance

B. AnD HV150KAI Balance

C. Fairbanks B90-5150 Balance

D. OHAUS WB25/1-20W Balance

E. Cole Parmer (51201-30) and Thermolyne (S25535) Stirrers

F. Sampling devices, such as steel scoops, drum samplers, etc.

G. Erlyenmeyer flasks, beakers, carboys and other appropriate glassware.

H. Production Solution Labels.

Safety:

Protective equipment, such as gloves, safety glasses, lab coats, and respirators should be worn when handling chemicals according to MSDS guidelines.

Raw Material Solutions Preparation Procedure:

To Hydrochloric Acid, 1364.2 g (±5.5 g) add 1364.2 g (±5.5 g) of USP Purified water. Stir until the solution is clear.

To Aluminum Sulfate Hexadecahydrate, 1779.1 g (±7.0 g) add 2548.9 g (±10.0 g) of USP Purified water. Stir until the solution is clear.

To Zinc Chloride, 7384.6 g (±30.0 g), add 2786.7 g (±11.0 g) of USP Purified water. Stir until the solution is clear.

To Potassium Dichromate, 2101.9 g (±8.0 g), add 25203.8 g (±100 g) of USP Purified water. Stir until the solution is clear.

To Sodium Thiosulfate Pentahydrate, 1526.6 g (±6.0 g), add 2043.6 g (±8.0 g) of USP Purified water. Stir until the solution is clear.

To Copper Sulfate Pentahydrate, 509.7 g (±2.0 g), add 1613.1 g (±6.0 g) of USP Purified water. Stir until the solution is clear.

To Sulfuric Acid, 600.0 g (±2.0 g), add 600.0 g (±2.0 g) of USP Purified water. Stir until the solution is clear.

To Sodium Chloride, 70.4 kg (±250 g), add 234.4 kg (±850 g) of USP Purified water. Stir until the solution is clear.

Synthesis

Synthesis Equipment and Supplies:

LFE Control Panel (3000)

20 gallon Jacketed Glass Lined Purification Tanks with lid (E71224)

Two 100 gallon Jacketed Glass Lined Purification Tank with lids (P1, PT-001)(P2, L-13621)

FTS Recirculating Cooler (RC96CO32) and 500 gallon Cold Storage Tank (500CST)

Three Caframo Mixers (BDC-1850) (R1, 18500961)(P1, 18501148) (P2, 18501173) with shaft and impeller Lightning Mixer (L1U08) (201550)

Three Heat Exchangers (Gardner Machinery) (R1, 01960763) (P1, 01960764) (P2, 08950727)

Three 12 KW Jacket Fluid recirculators (Watlow, BLC726C3S 20)

Three Recirculation Pumps (Sta-Rite, JBHD-62S, C48J2EC15)

Masterflex Digital Peristaltic Pump (A94002806)

Masterflex Peristaltic Pump (L95003320)

Cole Parmer Peristaltic Pump (B96002074)

Neutsche Filtration unit (70-2038, 43421-1)

Two Buchner Filtration Units (Z11,624-6, Z10,441-8)

Siemens Vacuum Pump (F2BV2)

60 Gallon Glass Lined Collection Tank with lid (86854, E164-1186)

Air Compressor (DF412-2) (9502312538)

Flow Controller (3-5500) (69705069190)

Six Batch Controllers (3-5600) (#1, 69705069191, #2, 69705069199, #3, 69705069194, #4, 69705058829, #5, 69705058805, #6, 69705069195)

Six Flow Sensors (#1, 69704295165, #2, 69704024995, #3, 69704024994, #4, 69704025027, #5, 69612178606, #6, 69703120990)

Four Diaphragm Pumps (M1)

Four Surge Suppressors (A301H) (#2, 15557, #3, 15561, #4, 15558, #5, 15559)

Four Air Regulators (CFR10)

Four Solenoid Valves (used with air regulators)

Four Low Flow Sensors (FS-500)

Three Solenoid Valves (EASM5V16W20)

Air Filter/Regulator (T1R)PTFE/F06R113AC

Filter media, Polypropylene (7211-1)

Filter media, Whatman Grade 52

PharMed tubing (−18, −82, −90)

pH Meter; Hanna 9321 (1303675) & Orion 620 (001911)

Spectrophotometer 20 (3MU7202070)

Fisher Scientific Vacuum Oven (9502-033)

VWR 1370 FM forced air oven (1370FM)

Dust/Mist Respirator

Thomas Wiley Laboratory Mill (3375-E10)

Patterson-Kelley Blender (Blendmaster, C416578)

OHAUS TS4KD Balance

OHAUS IP15KS Balance

Mettler AG 104 Balance

AnD HV150KA1 Balance

Fairbanks H90-5150 Balance

OHAUS AS123 Printer

OHAUS AS142 Printer

AD-8121 Multifunction Printer

Citizen iDP 3540 Dot Matrix Printer

Hewlett Packard HPLC (1050)

Ultrasonic Cleaner (8892-DTH, QCC9601 005C)

Type R Thermocouple Temperature Recorder (KTx, 6292753, 6355146)

Erlenmeyer Flasks (8L, 6 L, 4 L, 1 L)

Beakers (8L, 6L, 500 mL, 250 mL)

Carboys (4L, 10L, 50 L)

HDPE Drums (55 gallon, 100 gallon)

Volumetric Flasks (100 μL)

Plastic Funnel

Pastuer Pipettes & Bulbs and Volumetric Pipettes (10 mL, 5 mL) & Bulb

Bellows (25 mL, 50 mL)

Weigh Paper

Spatulas

Packaging Material (containers, lids, labels)

Raw Material Solutions

Synthesis: Step 1.

Synthesis of 2-amino-5-dimethylaminophenyl thiosulfonic acid:

Check the integrity of the USP water system. To the reactor add the weighed USP Grade Purified Water (28,000 g±100.0 g) and stir at 190±10 RPM.

Add N,N-dimethyl-1,4-phenylenediamine (5.128 mol, 720.0 g±3.0 g). The material should be added as a powder (no lumps). Stir 10 minutes (±5 minutes).

Add hydrochloric acid (6 N, 1136.9 g±5.0 g). Stir 15 minutes (±5 minutes).

Take a reaction mixture sample of approximately 10 mL using a plastic sampling device. Check the pH. The pH must be 2.8–3.8 @ 25° C. ±5° C.

Add aluminum sulfate hexadecahydrate solution (4328.0 g ±21.0 g). Stir 10 minutes (±5 minutes) at 275±10 RPM.

Add zinc chloride solution (3641.5 g±18.0 g). Cool to 4° C.±1° C.

Once the temperature (PV1) is 4° C.±1° C. add potassium dichromate solution (6532.4 g±32.0 g) over a 20 minute period (±5 minutes). When addition is complete stir 20 minutes (±5 minutes).

While maintaining the temperature at less than about 10° C., add sodium thiosulfate pentahydrate solution (3570.2 g±18.0 g). Stir the solution at 10° C. for 30 minutes (±5 minutes).

Change the Set Point to 60° C. When the temperature (PV1) reaches 60.0° C.±3.0° C. allow the reaction mixture to stir 5 minutes (±3 minutes) and change the Set Point on the LFE controller to 10.0.

Once the temperature has reached 13.0° C.±2.0° C., check the pH. The pH must be 3.1–4.1 @ 25° C.±5° C.

Synthesis: Step 2.

Synthesis of Indamine Thiosulfonic Acid

Weigh out o-toluidine (604.4 g±2.5 g) and cool to 18° C. ±3° C. in an ice bath. Add hydrochloric acid (6 N, 1230.7 g±5.0 g) to the o-toluidine slowly. Remove the o-toluidine hydrochloride from the ice bath and allow the solution to cool to 38° C.±3° C. Add the solution to the reaction mixture and stir 5 minutes (±3 minutes).

Add potassium dichromate solution (6532.4 g±32.0 g) over a 20 minute period (±5 minutes). When addition is complete stir 10 minutes (±5 minutes).

Change the controller Set Point (SP1) to 60.0. Once the reaction mixture temperature reaches 60.0° C.±3° C. allow the mixture to stir 25 minutes (±5 minutes). A precipitate will form consisting of a green indamine.

Synthesis: Step 3.
Synthesis of Zinc Chloride Double Salt:

Set the LFE controller Set Point to 7.0. Once the reaction mixture temperature reaches 10.0° C.±3° C. add potassium dichromate solution (6532.4 g±32.0 g) over a 20 minute period (±5 minutes). When addition is complete stir 20 minutes.

Add potassium dichromate solution (5225.9 g±26.0 g) over a 20 minute period (±5 minutes). When addition is complete stir 20 minutes (±5 minutes).

Add zinc chloride solution (3641.5 g±18.0 g). Stir 20 minutes (±5 minutes) at 350±10 RPM.

Add copper sulfate pentahydrate (2122.8 g±10.0 g). Stir 15 minutes (±5 minutes).

Change the controller Set Point (SP1) to 100.0. Once the reaction mixture temperature reaches 67.0° C.±3° C. begin to add sulfuric acid solution to pH 2.9±0.3 by adding aliquots (500 mL, 250, 125 mL, etc.). Stir for 5 to 10 minutes after each addition and check pH.

Once the reaction mixture temperature reaches 100.0° C.±3° C. allow the mixture to stir 35±5 minutes.

Change the controller Set Point (SP1) to 35.0. When the reaction mixture temperature reaches 70.0° C.±3° C., change the controller Set Point (SP1) to 2.5. Cool to 2.5° C. in 4 hours and Hold at 2.5° C.±2.0° C. for 4 to 18 hours.

Purification: Step 1

Filter the reaction mixture through suitable filter media (Whatman Grade 52).

When the reactor is empty weigh out 24.0 kg±150.0 g of 30% NaCl solution and add 24.0 kg±150.0 g of USP water. Close the reactor bottom valve and add the 15% NaCl solution to the reactor. Stir the solution briefly. When the filtration is complete add the NaCl solution to the filtration unit to rinse the filter cake.

Check the 100 gallon glass lined, jacketed purification tank # 1 condition and make certain the tank is clean and equip the tank with a HDPE lid, Caframo stirrer, stir shaft, propeller and thermocouple probe inserted into a plastic thermocouple well. Check that the bottom valve is off and the outlet is capped.

Weigh out 190.0 kg±1.0 kg of USP water into a HDPE container and transfer the water to Purification Tank 1. Stir the mixture at 350 RPM. Once the NaCl wash of the filter cake is complete add the filter cake to Purification Tank 1 while stirring.

Stir the mixture 2 to 4 hours.

Set the Purification Tank 1 LFE controller to 75.0 (SP1).

When the mixture temperature (PV1) reaches 75.0° C.±3° C. change the Set Point on the controller to 40.0.

Allow the mixture to stir at 40° C. and 350 RPM for 12 to 36 hours.

Take a sample (through the bottom valve) of approximately 50 mL. Measure 1.0 mL of the sample with a 1.0 mL pipette and dilute to 100 mL in a volumetric 100 mL flask. Then take 10.0 mL of this solution with a 10.0 mL pipette and dilute to 100 mL in a volumetric 100 mL flask. Measure the absorbance of this sample using the spectronic 20+. The absorbance of the sample should be $\geq 0.220$.

Purification: Step 2

Filter the mixture through filter media in the filtration unit. Collect the filtrate into a Tared HDPE container with lid.

Equip the 100 gallon glass lined, jacketed purification tank 2 with a lid, Caframo stirrer, stir shaft, propeller and thermocouple probe inserted into a plastic thermocouple well.

Into a clean HDPE container weigh out a quantity of 30% NaCl solution equal to the solution volume recorded above using the following formula:

$$(mL\ of\ soln)(116.91\ g\ NaCl\ soln/100.0\ mL\ NaCl\ soln) = g\ of\ NaCl\ soln$$

Sample 10 mL of the filtrate and check the pH. The pH must be 3.0–4.0. Transfer the filtrate to Purification Tank 2. Stir the solution at 350 RPM.

Add zinc chloride solution (1636.3 g±6.5 g)

Transfer the NaCl solution (by weight) to Purification Tank 2.

Set the Purification Tank 2 LFE controller to 75.0 (SP1).

When the mixture temperature (PV1) reaches 75.0° C.±3° C. change the Set Point on the controller to 5.0.

Cool to 5° C. in 6 hours and Hold at 5° C.±4.0° C. for 4 to 24 hours.

Processing
i. Filter

Filter the mixture through tared filtration media (Whatman Grade 52) in the filtration unit Weigh out 12 kg±50 g of 30% sodium chloride solution and dilute with 12 kg±50 g of USP water. Wash the filter cake with the 15% sodium chloride solution by adding the solution directly to the buchner. When the filtration is complete carefully remove the filter paper containing the product.

ii. Dry

Place the purified complex reaction product in the oven and dry at 50.0° C.±3.0° C. for 5±1 hours.

Remove the complex product from the forced air oven and place in the Vacuum Oven. Dry at 45.0° C.±3.0° C. @ 28" Hg±2" Hg for 10±2 hours.

iii. Grind

Install the 0.5 mm screen to the Thomas Wiley Laboratory Mill. Attach a clean container to the delivery chute. The chamber door must be closed and latched.

Close the sliding shutter at the bottom of the hopper, remove the hopper lid and add the dried complex product. Replace the hopper lid. Turn the mill ON and open the sliding shutter slightly. Feed product into the mill chamber slowly enough so that the mill does not slow down or become jammed.

Once the grinding is complete carefully remove the container from the delivery chute.

v. Blend

Transfer the product to the Patterson-Kelly Lab Blender container and close the lid. Set the timer to 15 minutes ±5 min.

HPLC Procedure for Isolation and Separation

This example describes a suitable HPLC procedure for isolating and separating the novel compounds of the present invention from the dried, ground and blended complex product prepared as described above.

A. Instruments and Equipment
  1. HPLC Chromatographic Procedures
    a. HP1100 EPLC Chromatographic System
    b. HP1100 Diode-array detector
    c. HP1100 Quaternary HPLC pump
  2. Fraction Collection and Purification
    a. ISCO Foxy Jr., 10 Channel fraction collector
    b. Büchi, model R-124 rotary evaporator
    c. Sep-pak cartridge, $C_{18}$, Varian
  3. Mass Spectral Analyses
    a. Electron Impact/Mass Sepcetrometry (EI-MS)
      1. MS Instrument: VG Analytical ZAB 2-SE
      2. Source temperature: 200° C.
      3. Electron Voltage: 70 ev
      4. Sample probe: solid probe
      5. Probe temperature: 280° C.
    b. Liquid Chromatography/Mass Spectrometry (LC-MS)
      1. HP1100 Binary pump with vacuum degasser
      2. Solvent A: water:ACN (88:12) v/v containing 0.1% TEA
      3. Solvent B: water:ACN (1:1) v/v containing 0.1% TEA
      4. Gradient: 0% solvent B raised to 30% solvent B in 18 minutes; raised to 100% solvent B after 27 minutes, hold 3 minutes
      5. Flow rate: 1.5 mL/minute
      6. Column: Water Symmetry $C_{18}$ Column 4.6 mm×250 mm,5 µm)
      7. Column temperature: 40° C.
      8. Detector: Variable wavelength UV, 290 nm
      9. MS Instrument: VG Bio-Q triple quadrupole mass spectrometer
      10. Operation mode: Postivie electrospray ionization (+ESI) mode
      11. Source temperature: 80° C.
    c. Fast Atom Bombardment (FAB-MS)
      1. MS Instrument: VG Analytical ZAB 2-SE
      2. Sample input: Cesium ion gun
      3. Data system: VH Analytical 11-250J with PDP 11/73
    d. Electrospray Mass Spectrometer (ESI-MS)
      1. MS Instrument: VG Biotech Bio-Q with quadrupole analyzer
      2. Operation mode: negative ion direct unfusion
      3. Injection volume: 50–75 µL
      4. Elution solvent: 50% aqueous ACN containing 0.1% FA
      5. Flow rate: 10 µL/minute
    e. Electrospray MS/MS (ESI-MS/MS)
      1. MS Instrument: VG Quattro II Bio-Q triple quadruople analyzer
      2. Collision gas: argon
      3. Sample aliquot: 50–75 µL
      4. Elution solvent: 50% aqueous ACN containing 0.1% TFA
      5. Flow rate: 10 µL/minute
    f. High Resolution Mass Spectrometer (ER-MS)
      1. MS Instrument: VG Analytical ZAB 2-SE
      2. Sample input: Cesium ion gun
      3. Data system: VH Analytical 11-250J with PDP 11/73
  4. Nuclear Magnetic Resonance Spectrometry (NMR)
    a. 400 MHz Varian Inova NMR
  5. X-ray Diffraction Single Crystal Analyses
    a. Nonius CAD4, Model 586, automated single crystal diffractometer
    b. Cu X-ray tube, fine focus, ($\lambda$=1.5418 Å)
    c. Random orientation photographic attachment, Polaroid, Model 57-3
    d. EXPRESS data collection software
    e. MOLEN data interpretation software
B. Chemincal, Reagent, and Standards
  1. Chemicals and Reagents
    a. Acetonitrile (ACN), HPLC grade
    b. Methanol (MeOH), EPLC grade
    C. Chloroform ($CHCl_3$), HPLC grade
    d. Glacial acetic acid (GAA), ACS grade
    e. Hydrochloric acid (HCI), ACS grade
    f. Milli-Q water
    g. Triethylamine (TEA), HJPLC grade
    h. Ammonium acetate, AR grade
    i. Sodium hydroxide (NaOH) pellets, reagent grade
    j. Nitrogen gas, zero grade
    k. Methanol, deuterated ($d_4$-MeOH)
    l. Dimethyl sulfoxide, deuterated ($d_6$-DMSO)
    m. Water, deuterated ($D_2O$)
    n. Hydrochloric acid, deuterated (DCI)
    o. Sodium tetraphenylborate, reagent grade Initial Preparative HPLC System 2 for Fraction Collection of Compounds Initial Fraction Collection Aqueous Diluent—Prepare a solution of 0.1 M acetic acid and adjust the pH to 6.1±0.1 with NaOH.

Mobile Phase A—88:12 Aqueous Diluent: ACN

Mobile Phase B—50:50 Aqueous Siluent: ACN

Sample Preparation: Prepare a 15 mg/mL solution of the dried, blended complex reaction product in aqueous diluent. Load the solution in 30 to 40 mL aliquots onto separate 10 g $C_{18}$ SPE cartridges, wash with approximately 20 mLs of aqueous diluent and then wash with approximately 10 mLs of water. Elute with approximately 10 mLs of 0.01 N BCI in MeOH. Rotary evaporate the cleaned sample to dryness and redissolve in aqueous diluent.

Chromatographic System: An AP 1100 EPLC system with a column heater is equipped with a 7 µm, 30.0 cm×7.8 mm $C_{18}$ column and a suitable UV detector for detection at 290 nm and diode array, the flow rate is set for 5.0 mL/minute and the column temperature for 20° C. The following gradient elution is used:

| | % Mobile Phase | |
|---|---|---|
| Time (min.) | A | B |
| 0 | 80 | 20 |
| 15 | 60 | 40 |
| 15.1 | 0 | 100 |
| 25 | 0 | 100 |
| 25.1 | 80 | 20 |

Procedure: 900 μL aliquots of the sample are injected onto the chromatographic system and the peaks of interest are collected using a multi-channel fraction collector. Once all of the fractions are collected, each fraction is rotary evaporated to remove most of the ACN, then concentrated on a $C_{18}$ SPE cartridge, washed with water, and eluted with approximately 5 mL of 0.01 N HCI in MeOH. Rotary evaporate the eluant to dryness and set aside for further purification.

Final Fraction Collection
Mobile Phase A—88:12 0.1% TEA:ACN
Mobile Phase B—50:50 0.1% TEA:ACN
Sample Preparation: Prepare solutions of the dried fractions from the initial fraction collection and dilute with Mobile Phase A.
Chromatographic System: An HP1100 HPLC system with a column heater is equipped with a 7 μm, 30.0 cm×7.8 mm $C_{18}$ column and suitable UV detector for detection at 290 nm and diode array, the flow rate is set for 5.0 mL/minute, and the column temperature for 30° C. The following gradient elution is used:

| | % Mobile Phase | |
|---|---|---|
| Time (min.) | A | B |
| 0 | 73 | 27 |
| 8 | 70.6 | 29.4 |
| 8.1 | 45 | 55 |
| 9 | 45 | 55 |
| 16 | 25.5 | 74.5 |
| 16.1 | 73 | 27 |

Procedure: 200 μL aliquots of the sample are injected onto the chromatographic system and the peaks of interest are collected using a multi-channel fraction collector. Once all of the fractions are collected, each fraction is initially rotary evaporated to remove most of the ACN, then concentrated on a $C_{18}$ SPE cartridge, washed with water, and eluted with approximately 5 mL of 0.01 N HCI in MeOH. The fractions are then brought to dryness under a stream of dry nitrogen and set aside to perform analyses for identification.

Compound IV Characterization
Separation and Isolation
Compound IV is isolated using a semi-reparative HPLC method. The fraction is collected, most of the ACN is removed by rotary evaporation, and the fraction is further concentrated using a $C_{18}$ SPE cartridge, washed with water, and eluted with approximately 5 mL of 0.01 N HCI in MeOH. The fraction is then bought to dryness under a stream of dry nitrogen. A portion of the material is redissolved in a mobile phase and injection on the HPLC system to determine the purity of the fraction. This injection of Compound IV shows a purity of about 95% and 8.2 mg is tested by NMR.

Mass Spectral Analyses
Preliminary LC-MS mass spectral data of the ground, blended complex reaction product indicates that the molecular weight of Compound IV is approximately 375.3 m/z. Further HR-MS studies using fractions collected from the LC-MS indicate a mass of 375.1655 m/z and a molecular formula of $C_{22}H_{23}N_4S_1$ for compound IV. The daughters of the 375 m/z parent ion of Compound IV are examined using positive ESI-MS/MS. The fragmentation pattern shows the predominant losses of 16 amu and 44 amu, from the molecular ion of Compound IV shows the structure of Compound IV. This Compound and its N- and N,N-dymethylated derivatives, Compounds V and VI are formed from a secondary reaction of the parent compound (TBO) and excess starting material O-toluidine.

Compound I Characterization
Separation and Isolation
Compound I is isolated using the semi-reparative HPLC method. The fraction is collected, most of the ACN is removed by rotary evaporation, and the fraction is further concentrated using a $C_{18}$ SPE cartridge, washed with water, and eluted with approximately 5 mL of 0.01 N HCI in MeOH. The fraction is then brought to dryness under a stream of dry nitrogen. A portion of the material is redissolved in mobile phase and injected on the HPLC system to determine the purity of the fraction. This injection of Compound I shows a purity of about 95% and 18.9 mg is tested by NMR.

Mass Spectral Analyses
Preliminary LC-MS mass spectral data of the dried, blended complex reaction product indicates that the molecular weight of Compound I is approximately 284.1 m/z. Further HR-MS studies using fractions collected from the LC-MS indicate a mass of 284.1223 m/z and a molecular formula of $C_{16}H_{18}N_3S_1$ for Compound I. The daughters of the 284 m/z parent ion of Compound I are examined using positive ES1-MS/MS. The proposed structure and fragmentation pattern showing the predominant losses of 16 amu, 30 amu, and 59 amu from the molecular ion yield the structure of Compound I. Compound I and its N- and N,N-dymethylated derivaties, Compounds II and II are formed from a free radical scavenging of a methyl group from another demethylated molecule onto the corresponding parent TBO isomer.

Compounds II, III, V and VI are isolated and characterized by the procedures described above for isolation and characterization of Compounds VI and I.

Example 2

Clinical Testing Protocol
Preparation of Clinical Test Solutions
This example illustrates the use of each of the products of Example 1 in the identification of oral dysplasia.

Compound I, raspberry flavoring agent (IFF Raspberry IC563457), sodium acetate trihydrate buffering agent and $H_2O_2$ (30% USP) preservative (See U.S. Pat. No. 5,372, 801), are dissolved in purified water (USP), glacial acetic acid and SD 18 ethyl alcohol, to produce a test solution, having the composition indicated in Table A:

TABLE A

| Component | Weight % |
|---|---|
| Compound I | 1.00 |
| Flavor | .20 |
| Buffering Agent | 2.45 |
| Preservative | .41 |

TABLE A-continued

| Component | Weight % |
|---|---|
| Acetic Acid | 4.61 |
| Ethyl Alcohol | 7.48 |
| Water | 83.85 |
| | 100.00 |

Pre-rinse and post-rinse test solutions of 1 wt. % acetic acid in purified water, sodium benzoate preservative and raspberry flavor are prepared.

Clinical Protocol

The patient is draped with a bib to protect clothing. Expectoration is expected, so the patient is provided with a 10-oz. cup, which can be disposed of in an infectious waste container or the contents of which can be poured directly into the center of a sink drain, to avoid staining the sink. Environmental surfaces or objects which might be stained are draped or removed from the test area.

A visual oral cancer examination is conducted, without using any instruments which might cause nicks or cuts of soft tissues. Notations are made of the pre-staining appearance of soft tissues and teeth.

The patient rinses the oral cavity with approximately 15 ml. of the pre-rinse solution for approximately 20 seconds and expectorates, to remove excess saliva and provide a consistent oral environment. This step is then repeated with additional pre-rinse solution.

The patient then rinses and gargles with water for 20 seconds and expectorates.

The patient then rinses and gargles with 30 ml. of the test solution for one minute and expectorates.

The patient then rinses with 15 ml. of the post-rinse solution for 20 seconds and expectorates. This step is then repeated.

The patient then rinses and gargles with water for 20 seconds and expectorates. This step is then repeated.

Observations of the oral cavity are then made, using appropriate soft-tissue examination techniques, including retraction, well-balanced lighting and magnification, if necessary. The location, size, morphology, color and surface characteristics of suspect lesions, that have retained blue coloration are made and recorded.

In order to reduce false positives, the patient is brought back after 10–14 days for a repeat of the above protocol. This period allows time for healing of any ulcerative or traumatic lesion or irritating etiology at the time of the first examination. A positive stain after the second examination of a suspect area detected in the first examination is considered an indication of cancerous or precancerous tissue and a biopsy is made to confirm this conclusion.

Early erythroplastic lesions stain blue, often in a stippled or patchy pattern. However, it normal for the Stain to be retained by the irregular papiliar crevices on the dorsum of the tongue, which is not a positive indication. Other areas which retain blue stain, but are not regarded as positive include dental plaque, gingival margins of each tooth, diffuse stain of the soft palate because of dye transferred from the retained stain on the dorsum of the tongue, and ulcerative lesions which are easily distinguished. In all instances, where a lesion is highly suspect, but does not stain positively with this test, it is nevertheless imperative that a biopsy be taken.

Examples 3–7

The procedures described above are repeated except that Compounds II, III, IV, V and VI are employed instead of Compound I. Similar results are obtained.

Having described my invention in such terms as to enable those skilled in the art to understand and practice it and, having identified the presently preferred best modes thereof, I claim:

1. A compound having the structural formula

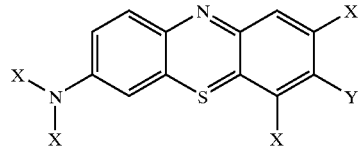

wherein X is hydrogen, methyl or Y; Y is —NH—R; and R is

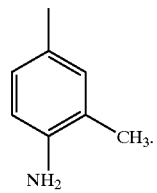

2. The compound having the structural formula

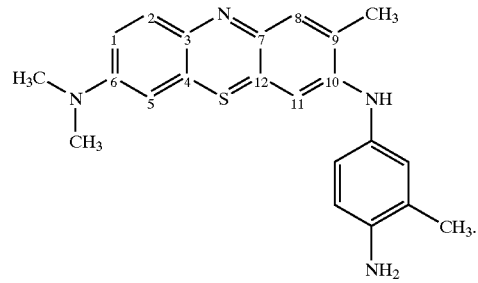

3. The compound having the structural formula

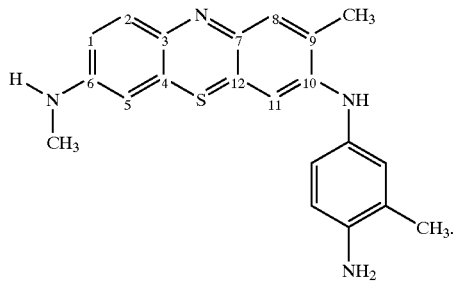

4. The compound having the structural formula

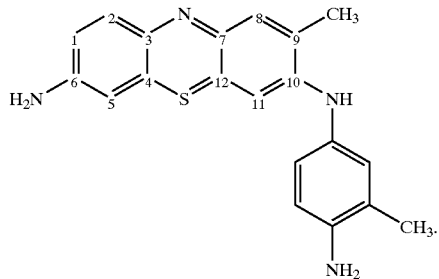

5. In a method for detecting dysplastic tissue including the step of applying to epitheleal tissue a biological stain composition which selectively stains dysplastic tissue, the improvement comprising applying a compound having the structural formula of claim 1.

* * * * *